United States Patent
Muehlbauer

(10) Patent No.: US 11,684,282 B2
(45) Date of Patent: Jun. 27, 2023

(54) SYSTEMS AND METHODS FOR EVALUATING BLOOD CIRCULATION AND EARLY DETECTION OF CARDIOVASCULAR ISSUES

(71) Applicant: AVACEN, INC., San Diego, CA (US)

(72) Inventor: Thomas G. Muehlbauer, San Diego, CA (US)

(73) Assignee: AVACEN, INC., San Diego, CA (US)

( * ) Notice: Subject to any disclaimer, the term of this patent is extended or adjusted under 35 U.S.C. 154(b) by 662 days.

(21) Appl. No.: 15/887,951

(22) Filed: Feb. 2, 2018

(65) Prior Publication Data

US 2018/0220898 A1    Aug. 9, 2018

Related U.S. Application Data

(60) Provisional application No. 62/454,336, filed on Feb. 3, 2017.

(51) Int. Cl.
*A61B 5/026* (2006.01)
*A61B 5/0205* (2006.01)
(Continued)

(52) U.S. Cl.
CPC .......... *A61B 5/026* (2013.01); *A61B 5/02007* (2013.01); *A61B 5/02055* (2013.01);
(Continued)

(58) Field of Classification Search
CPC ... A61B 5/01; A61B 5/02007; A61B 5/02055; A61B 5/026; A61B 2017/00084;
(Continued)

(56) References Cited

U.S. PATENT DOCUMENTS 1,399,095 A   12/1921   Webb, Sr.
1,740,624 A   12/1929   Peel
(Continued)

FOREIGN PATENT DOCUMENTS

EP   0 926 980 A2   7/1999
JP   2008-155007    7/2008
(Continued)

OTHER PUBLICATIONS

Shrivastava, D., and Vaughan, J. T. (Jun. 5, 2009). "A Generic Bioheat Transfer Thermal Model for a Perfused Tissue." ASME. J Biomech Eng. Jul. 2009; 131(7): 074506. (Year: 2009).*
(Continued)

*Primary Examiner* — Nathan J Jenness
*Assistant Examiner* — Michael A Catina
(74) *Attorney, Agent, or Firm* — Eversheds Sutherland (US) LLP; Nicola A. Pisano; Albert K. Heng

(57) ABSTRACT

Systems and methods are provided for blood circulation evaluation by providing a measurement device collection in communication with a thermal exchange device comprising an appendage chamber having a thermal exchange member. The measurement device collection may measure patient information such as height, weight, temperature, pulse, and/or blood pressure, and transmit the patient information to the thermal exchange device to estimate patient blood volume based on the patient information. Blood flowing through the arteriovenous anastomosis (AVA) of the appendage may be heated or cooled at the thermal exchange member for therapeutic application of thermal energy to adjust blood viscosity in the human to alleviate symptoms associated with a number of autoimmune, circulatory, neurological, lymphatic, and endocrinal maladies. The thermal exchange device may calculate a patient circulation rating based on the estimated blood volume, thermal transfer
(Continued)

energy over a specific time period or thermal transfer at various locations throughout the body, and a baseline circulation rating, and generate an alert if the patient circulation rating falls outside a predetermined threshold.

11 Claims, 7 Drawing Sheets

(51) Int. Cl.
    *A61B 5/00*         (2006.01)
    *A61B 5/02*         (2006.01)
    *A61B 5/0295*     (2006.01)
    *A61B 5/01*         (2006.01)
    *A61B 5/1171*     (2016.01)
(52) U.S. Cl.
    CPC .......... *A61B 5/0295* (2013.01); *A61B 5/6826* (2013.01); *A61B 5/6834* (2013.01); *A61B 5/7278* (2013.01); *A61B 5/01* (2013.01); *A61B 5/1171* (2016.02); *A61B 5/6838* (2013.01); *A61B 5/7275* (2013.01); *G01N 2800/50* (2013.01)
(58) Field of Classification Search
    CPC ...... A61F 2007/0029; A61F 2007/0039; A61F 2007/0239; A61F 2007/0086; A61F 2007/0096; A61H 9/0057; A61H 2201/0228
    See application file for complete search history.

(56) References Cited

U.S. PATENT DOCUMENTS

| | | | |
|---|---|---|---|
| 2,235,138 | A | 3/1941 | Billetter |
| 3,859,989 | A | 1/1975 | Spielberg |
| 4,329,997 | A | 5/1982 | De Yampert et al. |
| 4,735,195 | A | 4/1988 | Blum et al. |
| 5,027,795 | A | 7/1991 | Kato |
| 5,369,807 | A | 12/1994 | Cho et al. |
| 5,425,742 | A | 6/1995 | Joy |
| 5,637,076 | A | 6/1997 | Hazard et al. |
| 5,683,438 | A | 11/1997 | Grahn |
| 5,688,208 | A | 11/1997 | Plemmons |
| 5,693,004 | A | 12/1997 | Carlson et al. |
| 5,733,318 | A | 3/1998 | Augustine |
| 6,149,674 | A | 11/2000 | Borders |
| 6,287,252 | B1* | 9/2001 | Lugo .................... A61B 5/1112 128/903 |
| 6,315,696 | B1 | 11/2001 | Garrioch |
| 6,434,423 | B1 | 8/2002 | Ross |
| 6,602,277 | B2 | 8/2003 | Grahn et al. |
| 6,656,208 | B2 | 12/2003 | Grahn et al. |
| 6,673,099 | B2 | 1/2004 | Grahn et al. |
| 6,752,794 | B2 | 6/2004 | Lockwood et al. |
| 6,846,322 | B2 | 1/2005 | Kane et al. |
| 6,966,922 | B2 | 11/2005 | Grahn et al. |
| 6,974,442 | B2 | 12/2005 | Grahn et al. |
| 7,122,047 | B2 | 10/2006 | Grahn et al. |
| 7,160,316 | B2 | 1/2007 | Hamilton et al. |
| 7,169,119 | B2 | 1/2007 | Chan et al. |
| 7,182,776 | B2 | 2/2007 | Grahn et al. |
| 7,862,600 | B2 | 1/2011 | Grahn et al. |
| 7,972,287 | B2 | 7/2011 | Stewart et al. |
| 8,460,355 | B2 | 6/2013 | Cazzini et al. |
| 8,569,566 | B2 | 10/2013 | Blott et al. |
| 8,603,150 | B2 | 12/2013 | Kane et al. |
| 8,679,170 | B2 | 3/2014 | Muehlbauer et al. |
| 9,066,781 | B2 | 6/2015 | Muehlbauer et al. |
| 9,192,509 | B2 | 11/2015 | Muehlbauer et al. |
| 9,687,385 | B2 | 6/2017 | Muehlbauer et al. |
| 2001/0049546 | A1 | 12/2001 | Dvoretzky et al. |
| 2002/0151826 | A1 | 10/2002 | Ramey et al. |
| 2003/0004083 | A1 | 1/2003 | France |
| 2003/0040783 | A1 | 2/2003 | Salmon |
| 2003/0097163 | A1 | 5/2003 | Kane et al. |
| 2004/0015127 | A1 | 1/2004 | Silver et al. |
| 2005/0051174 | A1 | 3/2005 | Emerson |
| 2005/0103353 | A1 | 5/2005 | Grahn et al. |
| 2006/0111766 | A1 | 5/2006 | Grahn et al. |
| 2007/0060987 | A1 | 3/2007 | Grahn et al. |
| 2007/0088250 | A1 | 4/2007 | Silver et al. |
| 2007/0093730 | A1 | 4/2007 | Chan et al. |
| 2007/0112400 | A1 | 5/2007 | Hamilton et al. |
| 2007/0123962 | A1 | 5/2007 | Grahn et al. |
| 2007/0240247 | A1 | 10/2007 | Beck |
| 2008/0004549 | A1 | 1/2008 | Anderson et al. |
| 2008/0021531 | A1 | 1/2008 | Kane et al. |
| 2008/0034466 | A1 | 2/2008 | Zicarelli |
| 2008/0077201 | A1 | 3/2008 | Levinson et al. |
| 2008/0077205 | A1 | 3/2008 | Cazzini |
| 2008/0132816 | A1 | 6/2008 | Kane et al. |
| 2008/0132976 | A1 | 6/2008 | Kane et al. |
| 2008/0208088 | A1 | 8/2008 | Cazzini et al. |
| 2008/0249593 | A1 | 10/2008 | Cazzini et al. |
| 2008/0300515 | A1 | 12/2008 | Nozzarella et al. |
| 2009/0036959 | A1 | 2/2009 | Filtvedt et al. |
| 2009/0043237 | A1* | 2/2009 | Langley ............. A61M 1/3656 604/6.02 |
| 2009/0048649 | A1 | 2/2009 | Peret et al. |
| 2009/0112298 | A1 | 4/2009 | Jusiak et al. |
| 2009/0177184 | A1* | 7/2009 | Christensen ......... A61H 9/0092 604/506 |
| 2009/0240191 | A1 | 9/2009 | Loori et al. |
| 2010/0106199 | A1 | 4/2010 | Sawa et al. |
| 2010/0106230 | A1 | 4/2010 | Buchanan et al. |
| 2010/0152633 | A1 | 6/2010 | Rein et al. |
| 2010/0152821 | A1 | 6/2010 | Rein et al. |
| 2010/0262048 | A1 | 10/2010 | Shinomiya et al. |
| 2010/0280448 | A1 | 11/2010 | Lantz et al. |
| 2011/0000484 | A1 | 1/2011 | Melsheimer |
| 2011/0071465 | A1 | 3/2011 | Wang et al. |
| 2011/0092893 | A1 | 4/2011 | Demers et al. |
| 2011/0092894 | A1 | 4/2011 | McGill et al. |
| 2011/0098635 | A1 | 4/2011 | Helmore et al. |
| 2011/0106002 | A1 | 5/2011 | Helmore et al. |
| 2011/0125085 | A1 | 5/2011 | McGill et al. |
| 2011/0172749 | A1 | 7/2011 | Christensen et al. |
| 2012/0095420 | A1 | 4/2012 | Anderson et al. |
| 2012/0123322 | A1 | 5/2012 | Scarpaci et al. |
| 2012/0191022 | A1 | 7/2012 | Muehlbauer et al. |
| 2013/0165847 | A1 | 6/2013 | Scarpaci et al. |
| 2013/0184638 | A1 | 7/2013 | Scarpaci et al. |
| 2014/0257440 | A1* | 9/2014 | Muehlbauer ............ A61F 7/007 607/99 |
| 2017/0348142 | A1 | 12/2017 | Muehlbauer et al. |

FOREIGN PATENT DOCUMENTS

| | | |
|---|---|---|
| WO | WO-98/40039 A1 | 9/1998 |
| WO | WO-03/007804 A2 | 1/2003 |
| WO | WO-2004/046551 A1 | 6/2004 |
| WO | WO-2005/030101 A1 | 4/2005 |
| WO | WO-2012/012683 A1 | 1/2012 |
| WO | WO-2016/025438 A1 | 2/2016 |

OTHER PUBLICATIONS

Grahn, et al., Recovery from mild hypothermia can be accelerated by mechanically distending blood vessels in the hand, J. Appl. Physiol., 85(5):1643-1648 (1998).
PCT International Search Report and Written Opinion dated Sep. 26, 2014 in Int'l PCT Patent Application No. PCT/US2014/021355.
Communication Relating to the Results of the Partial International Search dated Apr. 23, 2018 in Int'l PCT Patent Appl. Serial No. PCT/US2018/016749.
International Search Report & Written Opinion dated Jun. 21, 2018 in Int'l PCT Patent Appl. No. PCT/US2018/016749, 14 pages.
International Search Report dated Oct. 14, 2011, in Intl PCT Patent Appl. No. PCT/US2011/044949, 5 pages.

(56) References Cited

OTHER PUBLICATIONS

Response to Written Opinion dated May 3, 2012 in Int'l PCT Patent Appl. No. PCT/US2011/044949, 4 pages.
Written Opinion dated Oct. 14, 2011 in Int'l PCT Patent Appl. No. PCT/US2011/044949, 7 pages.
U.S. Appl. No. 13/188,900 / U.S. Pat. No. 8,679,170, filed Jul. 22, 2011 / Mar. 25, 2014.
U.S. Appl. No. 13/794,413 / U.S. Pat. No. 9,192,509, filed Mar. 11, 2013 / Nov. 24, 2015.
U.S. Appl. No. 14/206,935 / U.S. Pat. No. 9,066,781, filed Mar. 12, 2014 / Jun. 30, 2015.
U.S. Appl. No. 14/774,691 / U.S. Pat. No. 9,687,385, filed Mar. 6, 2014 / Jun. 27, 2017.
U.S. Appl. No. 15/630,862, filed Jun. 22, 2017.

\* cited by examiner

SYSTEMS AND METHODS FOR EVALUATING BLOOD CIRCULATION AND EARLY DETECTION OF CARDIOVASCULAR ISSUES

CROSS-REFERENCE TO RELATED APPLICATIONS

This application claims the benefit of priority of U.S. Provisional Application Ser. No. 62/454,336, filed Feb. 3, 2017, the entire contents of which are incorporated herein by reference.

FIELD OF THE INVENTION

The present disclosure relates generally to therapeutic manipulation of mammalian thermoregulation.

BACKGROUND OF THE INVENTION

The body temperature of mammals is normally tightly controlled by an autonomic regulatory system referred to herein as the thermoregulatory system. A primary effector of this regulatory system is blood flow to specialized skin areas where heat from the body core may be dissipated to the environment. Normally, when body and/or environmental temperatures are high, the dilation of certain blood vessels favors high blood flow to these skin areas, and as environmental and/or body temperatures fall, vasoconstriction reduces blood flow to these skin areas and minimizes heat loss to the environment.

Strategic inducement of vasodilation and heat transfer in targeted portions of the body, such as the extremities, may exert positive therapeutic benefits in remote regions of the body. For example, manipulating heat transfer across the skin may change the core temperature of the mammalian body in response. Unfortunately, it may be difficult to induce such changes to an extent sufficient for therapy, given the human body's refined ability to thermoregulate to maintain temperature homeostasis or normothermia.

By applying heat and subatmospheric (negative) pressure to a hypothermic individual's skin, normothermia may be achieved (see, e.g., Grahn et al., "Recovery from mild hypothermia can be accelerated by mechanically distending blood vessels in the hand," J. Appl Physiol. (1998) 85(5): 1643-8). Other therapeutic applications for cooling the skin to achieve normothermia have also been described in U.S. Pat. No. 7,182,776 to Grahn.

Poor blood circulation may be indicative of cardiovascular issues such as cardiac arrhythmias, e.g., tachycardia, which may lead to stroke, myocardial infarction, and even death. Every year, billions of dollars are spent on evaluations, treatment, and drugs to mitigate or detect cardiovascular issues. Such drugs suffer from a variety of drawbacks including cost and side effects such as dizziness, headache, nausea, vomiting, chest pain, and irregular heartbeat. In addition, signs of cardiovascular issues may be overlooked, preventing the patient from seeking necessary medical attention before it is too late. Needless and expensive doctor's office and hospital evaluation visits tie up valuable medical resources.

In view of the foregoing drawbacks of previously known systems, it would be desirable to provide a robust and economical system to monitor blood circulation and detect at risk patients experiencing early signs of potential cardiovascular issues. It is also desirable to detect healthy patients in order to sidestep costly evaluations and risky treatments until the potential for cardiovascular issues can be firmly diagnosed.

SUMMARY OF THE INVENTION

In view of the foregoing drawbacks and cost savings, provided herein is a blood evaluation system designed primarily for home or medical office use to analyze a user's blood circulation in an easy-to-use, noninvasive manner. The blood evaluation system may store patient-specific treatment information for reviewing at a later time alongside current and previous treatment information such that negative trends, if any, may be detected early on. For example, the blood circulation analysis may be used to predict cardiovascular issues, e.g., cardiac arrhythmias, cardiac arrest, or myocardial infarction, based on the detected negative trends such that medical attention may be sought before the patient's cardiovascular system is jeopardized. Accordingly, the blood evaluation system may alert the user's doctor and/or the user (e.g., a visual/audible alert suggesting a doctor's visit) before the patient's health suffers further.

In accordance with one aspect of the present invention, the blood evaluation system includes an appendage chamber, a thermal exchange member, and a pressure source. The appendage chamber is sized and shaped to accept a human appendage, e.g., hand or foot, containing an arteriovenous anastomosis (AVA). The thermal exchange member is disposed within the appendage chamber and configured to selectively heat or cool blood flowing through the AVA. The pressure source is coupled to the appendage chamber and configured to apply negative pressure within the appendage chamber.

The system may include a non-transitory computer readable medium having instructions that, when executed by a processor, cause the processor to estimate a blood volume of a patient based on patient information comprising at least one of patient height, weight, age, gender, or fitness, apply and monitor thermal energy transfer to the appendage within the appendage chamber using the thermal exchange member, calculate a patient circulation rating based on the estimated blood volume and thermal energy transfer over a specific time period and/or at various locations throughout the body, compare the patient circulation rating with a baseline healthy circulation rating, and send an alert if the patient circulation rating falls outside a predetermined range.

In one embodiment, the system may include a display configured to display the patient circulation rating. The baseline circulation rating may be selected from a database stored within a memory of the processor based on the patient's estimated blood volume. The processor may also be configured to compare the currently measured patient circulation rating with one or more previously stored patient circulation ratings for the same patient based on patient identity to determine whether there is a negative trend. Accordingly, the processor may send an alert if a negative trend is determined.

In accordance with another aspect of the present invention, the system may include a measurement device collection operatively coupled to the processor, the measurement device collection configured to measure patient information comprising at least one of patient height, weight, temperature, pulse, and/or blood pressure. For example, the measurement device collection may include an ocular surface temperature sensor and/or one or more biometric patches. The measurement device collection may be operatively coupled to a data collection hub configured to generate a signal indicative of the measured patient information and transmit, e.g., wirelessly, the signal to the processor. The measurement device collection may also independently transmit patient information to the processor. In one embodiment, the data collection hub is also configured to generate a signal indicative of an estimated blood volume based on the measured patient information, such that the processor is configured to calculate the patient circulation rating based on the signal indicative of estimated blood volume and thermal energy transfer over a specific time period and/or at various locations throughout the body. The system may further include a biometric patch for measuring temperature, wherein the processor is further programmed to direct a thermal exchange member to heat or cool to a temperature responsive to biometric patch data.

In accordance with one aspect of the present invention, the measurement device collection may be operatively coupled to a patient identifier configured to determine a patient identity. For example, the patient identifier may include a retinal scanner configured to receive a patient retina blood vessel pattern to determine patient identity, and/or a data entry interface or RFID reader configured to receive user input to determine patient identity.

In accordance with yet another aspect of the present invention, a method for evaluating blood circulation of a patient is provided. The method includes determining a patient identity, measuring patient information comprising at least one of patient height, weight, age, gender, or fitness, estimating a blood volume of the patient based on the measured patient information, applying and monitoring thermal energy transfer to an appendage of the patient, calculating a patient circulation rating based on the estimated blood volume and monitored thermal energy transfer over a specific time period and/or at various locations throughout the body, comparing the patient circulation rating with a baseline healthy circulation rating, and sending an alert if the patient circulation rating falls outside a predetermined range. The method may also include displaying the patient circulation rating.

In one embodiment, the method includes comparing the currently measured patient circulation rating with one or more previously stored patient circulation ratings for the same patient based on the patient identity to determine whether there is a negative trend, and sending an alert if the negative trend is determined.

DETAILED DESCRIPTION OF THE INVENTION

Figure 1A:
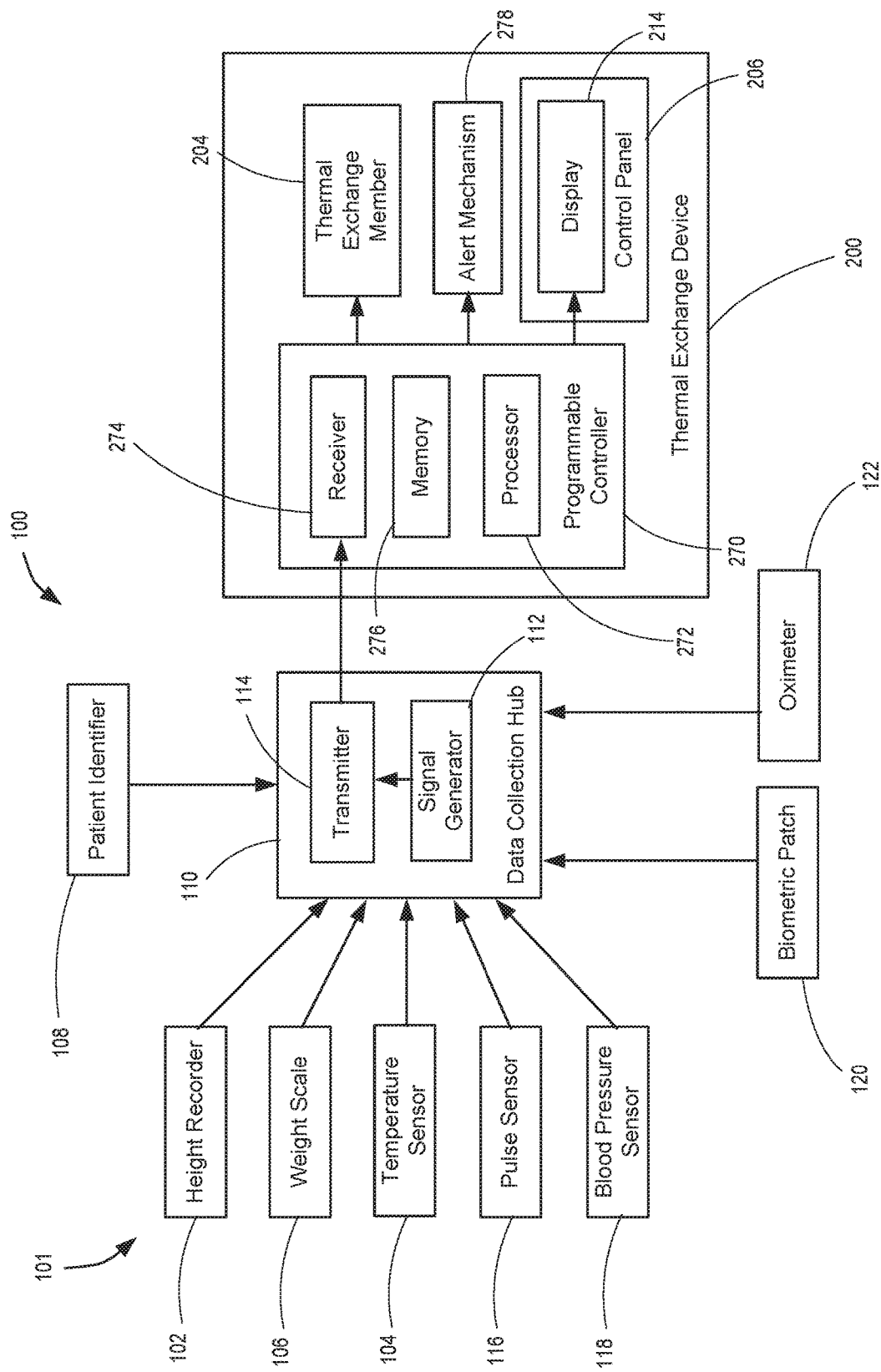
FIGS. 1A and 1B are a schematic view of exemplary blood evaluation systems constructed in accordance with one aspect of the present invention

The present invention provides systems and methods for applying thermal energy to a human at normothermia to increase microcirculation, while evaluating blood circulation to monitor patient receptiveness to the treatment and to predict cardiovascular issues. The methods and apparatus of the present invention are expected to also provide beneficial results in treating a number of common ailments, including improved healing of acute and chronic wounds, and relief from neurological and hormone-relating ailments as described in U.S. Pat. Nos. 8,679,170, 9,066,781, 9,192,509, and 9,687,385 to Muehlbauer, assigned to the assignee of the present invention, the entire contents of each of which are incorporated herein by reference.

In accordance with one aspect of the present invention, a blood circulation evaluation system is provided that includes a measurement device collection and a thermal exchange device. The measurement device collection preferably has one or more measurement devices. In one embodiment, the one or more measurement devices identifies the patient, measures patient information, e.g., height, weight, temperature, pulse, and/or blood pressure, and generates and transmits one or more signals indicative of the patient information to the thermal exchange device.

The thermal exchange device may be constructed as described in any of the aforementioned Muehlbauer patents and applications. For example, in one embodiment, the thermal exchange device provides a negative pressure environment that assists in maintaining vasodilation and enhances the transfer to energy to an arteriovenous anastomosis (AVA) vascular area of the palm of a human hand. The AVA vascular area may experience vasodilation from pre-treatment hyper-normothermia and/or heat delivered to the area from the thermal exchange member during treatment. This vasodilation increases the heat exchange between the thermal exchange member and the circulatory system by increasing blood flow and/or volume within the palm AVA's. An appendage chamber, e.g., box enclosure, clamshell, glove-like, boot-like, or sleeve-like chamber, may be used to provide a negative pressure environment while providing heating or cooling to an appendage using a thermal exchange system. While embodiments of the invention will be described further below with respect to a chamber sized and shaped to receive a hand, it is recognized that the appendage chamber may be adapted for use with other appendages containing an AVA suitable for the vasodilation methods described herein, such as vasculatures in the foot. The thermal exchange device may also monitor the thermal energy transfer to the AVA vascular area and/or one or more separate measurement devices, and evaluate and store patient treatment information for early detection of cardiovascular issues.

The aforementioned patents and applications to Muehlbauer provide systems and methods for applying thermal energy to a human at normothermia to increase or decrease blood viscosity to address a variety of medical conditions such as autoimmune, circulatory, neurological, lymphatic, and endocrinal maladies, and evaluating blood circulation based on thermal energy transfer and estimated patient blood volume.

Referring now to FIG. 1A, a schematic illustrating an exemplary blood evaluation system 100 for treating a condition constructed in accordance with one aspect of the present invention is described. Blood evaluation system 100 includes thermal exchange device 200 and measurement device collection 101. Blood evaluation system 100 also may include patient identifier 108, biometric patch 120, and oximeter 122. Thermal exchange device 200 includes thermal exchange member 204, control panel 206, display 214, alert mechanism 278, and programmable controller 270 having processor 272, receiver 274, and memory 276. Measurement device collection 101 may include a wheelchair base sized and shaped to permit a wheelchair to be positioned thereon.

Measurement device collection 101 may include, separately or together in a common housing, height recorder 102, temperature sensor 104, weight scale 106, pulse sensor 116, and/or blood pressure sensor 118, each in electrical communication with thermal exchange device 200 via data collection hub 110. As will be understood by a person having ordinary skill in the art, one or more of the devices of measurement device collection 101 may be coupled together and share a common housing, separate from the other devices of measurement device collection 101. Data collection hub 110 may be electrically coupled to the devices of measurement device collection 101, patient identifier 108, biometric patch 120, and oximeter 122 directly or wirelessly. For example, data collection hub 110 may include a network of servers accessible over the Internet, e.g., cloud computing. Accordingly, height recorder 102, temperature sensor 104, weight scale 106, pulse sensor 116, blood pressure sensor 118, patient identifier 108, biometric patch 120, and oximeter 122, each may have its own respective signal generator and transmitter for generating one or more signals indicative of the measured/input data, and transmitting the signal(s) wirelessly to data collection hub 110.

Data collection hub 110 may include signal generator 112 and transmitter 114, and may be electrically coupled to, and designed to receive data from the devices of measurement device collection 100, biometric patch 120, and/or oximeter 122. Data collection hub 110 may be programmed to estimate the patient's blood volume based on the collected patient data and to generate a signal indicative of the estimated blood volume. Patient data may include the patient's fitness level, e.g., whether the patient is muscular, thin, normal, or obese. Data collection hub 110 is designed to communicate the signal(s) to thermal exchange device 200.

Patient identifier 108 is designed to determine the identity of the patient and to electronically transmit information indicative of the patient's identity to data collection hub 110. For example, patient identifier 108 may include a retinal scanner designed to receive a patient retina blood vessel pattern to determine patient identity. The retinal scanner may be incorporated within eye goggles as part of measurement device collection 101. Alternatively, or in addition to, patient identifier 108 may include a data entry interface configured to receive user input to determine patient identity, e.g., the patient may enter identifying information such as a name, fitness level or identification number directly into the data entry interface of patient identifier 108. Patient identifier 108 alternatively may include a scanner that reads a bar code or QR code assigned to a patient that is maintained on the patient's paper file or an RFID transmitter on a patient-attached hospital bracelet. Upon determination of the patient's identity, patient identifier 108 may electronically transmit information indicative of the patient's identity to data collection hub 110, where it is temporarily stored pending further transmission, as described below.

Height recorder 102 is designed to digitally record a height of a patient and to electronically transmit information indicative of the patient's recorded height to data collection hub 110. Height recorder 102 may be constructed using digital distance measurement technology or using measurement technology known in the art, e.g., a smartphone. Temperature sensor 104 is designed to measure temperature of a patient and to electronically transmit information indicative of the patient's measured temperature to data collection hub 110. For example, temperature sensor 104 may include an infrared ocular sensor for measuring ocular surface temperature of the patient. The infrared ocular sensor may be incorporated within eye goggles as part of measurement device collection 101. In another embodiment, temperature sensor 104 may include an infrared tympanic temperature sensor. Temperature sensor 104 may be constructed in accordance with digital temperature reading technology known in the art. Weight scale 106 is designed to measure a weight of a patient and to electronically transmit information indicative of the patient's measured weight to data collection hub 110. Weight scale 106 may be constructed using digital measurement technology known in the art, e.g., as used in conventional analog and digital weight scales. In addition, pulse sensor 116 is designed to measure the pulse of the patient and to electronically transmit information indicative of the patient's recorded pulse to data collection hub 110, and blood pressure sensor 118 is designed to measure blood pressure of the patient and to electronically transmit information indicative of the patient's recorded blood pressure to data collection hub 110.

Biometric patch 120 is designed to measure skin temperature of the patient. For example, biometric patch 120 may include one or more biometric patches (e.g., biometric patch by Qualcomm Life, Inc., San Diego, Calif.) that may be used to noninvasively measure patient skin temperature at a specific location, e.g., the palm of the non-treatment hand, and to electronically transmit information indicative of the patient's measured temperature to data collection hub 110. Oximeter 122 is designed to noninvasively monitor a person's oxygen saturation at a specific location, e.g., on the non-treatment hand, and to electronically transmit information to data collection hub 110 for analysis.

Signal generator 112 is configured to generate one or more signals indicative of the data received from height recorder 102, temperature sensor 104, weight scale 106, patient identifier 108, pulse sensor 116, blood pressure sensor 118, biometric patch 120, and/or oximeter 122. Transmitter 114 is configured to transmit, e.g., wirelessly, one or more signals to receiver 274 of processor 270 of thermal exchange device 200.

As described above, each device of measurement device collection 101 may individually include its own signal generator and transmitter such that each device generates a signal indicative of the recorded measurement and transmits the signal to programmable controller 270 of thermal exchange device 200. Alternatively, the signals may be communicated to thermal exchange device 200 via a network of servers over the Internet, e.g., cloud computing.

Programmable controller 270 may be electrically coupled to, and programmed to control, the components of thermal exchange device 200 described above, e.g., thermal exchange member 204, control panel 206, display 214, and/or alert mechanism 278. The programmable controller of thermal exchange device 200 may include processor 272, e.g., one or more microprocessors, controllers, digital signal processors (DSPs), application specific integrated circuits (ASICs), field-programmable gate arrays (FPGAs), or equivalent discrete or integrated digital or analog logic circuitry, and the functions attributed to programmable controller 270 herein may be embodied as software, firmware, hardware, or any combination thereof. Programmable controller 270 may include memory 276, e.g., non-transitory computer readable media, for storing data related to use of thermal exchange device 200, such as user input, treatment times, treatment settings, detected errors, and the like.

Memory 276 may store program instructions that, when executed by processor 272 of programmable controller 270, cause programmable controller 270 and thermal exchange device 200 to provide the functionality ascribed to them herein, e.g., apply and monitor thermal energy transfer to an appendage of the patient within appendage chamber 202 using thermal energy member 204. Memory 276 of programmable controller 270 may also store a database of patient identities, such that upon determination of patient identity using patient identifier 108 and receiving a signal indicative of the patient identity via receiver 274, programmable controller 270 may evaluate and store patient treatment information based on patient identity. Each patient identity stored within memory 276 may contain information indicative of the patient's gender and/or age, and/or fitness level, previously inputted, e.g., via data entry interface of patient identifier 108. Memory 276 of programmable controller 270 also may store software downloaded thereon or implemented as a program product for controlling thermal exchange device 200 and/or data analysis. The contents of memory 276 may further be stored on a tangible storage device such as machine-readable medium, e.g., tape, compact disk (CD), digital versatile disk (DVD), blu-ray disk (BD), external nonvolatile memory device, USB, cloud storage, or other tangible storage medium.

Programmable controller 270 also may store in memory 276 therapy programs directed to treatment of specific maladies. For example, an embodiment of thermal exchange device 200 intended for use in a nursing home setting may include programs for increasing whole body circulation to address neurological ailments, such as migraine headaches, or circulatory issues, such as chronic wounds or reduced peripheral blood flow resulting from diabetes or immobility.

Monitoring programs may also reside in programmable controller 270 wherein the duration and/or parameters of treatment, e.g., amount of heat transfer from thermal exchange member 204, is determined by the change in temperature measured over time and/or at various locations throughout the body as indicated by thermal exchange device 200 and/or biometric patch 120. For example, thermal exchange device 200 may measure the time it takes to raise the temperature in the palm of the non-treatment hand of the patient by a delta of 12° F. as measured by biometric patch 120, and then compare that time with that required by a healthy individual with similar physical characteristics as stored in a database of baseline healthy circulation ratings. Similarly, thermal exchange device 200 may measure the time it takes to raise the temperature in the sole of the foot of the patient a delta of 10° F. as measured by biometric patch 120, and then compare that time with that required by a healthy individual with similar physical characteristics as stored in a database of baseline healthy circulation ratings.

In this context, thermal exchange device 200 may be used by a number of nursing home residents to provide relief from such ailments, and include preprogrammed therapeutic regimes (e.g., appropriate temperature adjustments for preselected durations) suitable for treating such residents. Preselected programs stored in thermal exchange device 200 may be loaded at the manufacturer, or generated using a suitable software program on a conventional personal computer and then uploaded to memory associated with programmable controller 270 via a data port, e.g., USB port or wirelessly via Bluetooth or WiFi. The data port further may be used to retrieve and/or store data on a tangible storage device related to use of thermal exchange device 200, such as user input, treatment times, treatment settings, detected errors, and the like.

Programmable controller 270 also may store in memory 276 patient treatment evaluation programs directed to evaluation of patient receptiveness to the treatment based on the monitored thermal energy transfer of the patient undergoing treatment or during surgery. For example, memory 276 may store a database of baseline healthy circulation ratings and/or patient temperature data. Each baseline circulation rating is calculated based on the blood volume and thermal energy transfer over a specific time period and/or at various locations throughout the body of a healthy person using thermal exchange device 200 for a treatment period.

For example, Table 1 below illustrates the baseline circulation ratings of healthy persons of age 56 and of age 57, each having a blood volume of 6100 mL, 6200 mL, 6300 mL, or 6400 mL, respectively.

TABLE 1

| Age | Milliliters Blood Volume (V) | At Plateau Joules/Infused (J)[2] | Biometric Patch Temperature Increase[3] | AHI[1]- Normal W/V |
|---|---|---|---|---|
| 56 | 6100 | 660 | Profile 1A | 0.1082 |
|  | 6200 | 672 | Profile 1B | 0.1084 |
|  | 6300 | 684 | Profile 1C | 0.1086 |
|  | 6400 | 694 | Profile 1D | 0.1088 |
| 57 | 6100 | 657 | Profile 2A | 0.1077 |
|  | 6200 | 669 | Profile 2B | 0.1079 |
|  | 6300 | 681 | Profile 2C | 0.1081 |
|  | 6400 | 693 | Profile 2D | 0.1083 |

Figure 6:
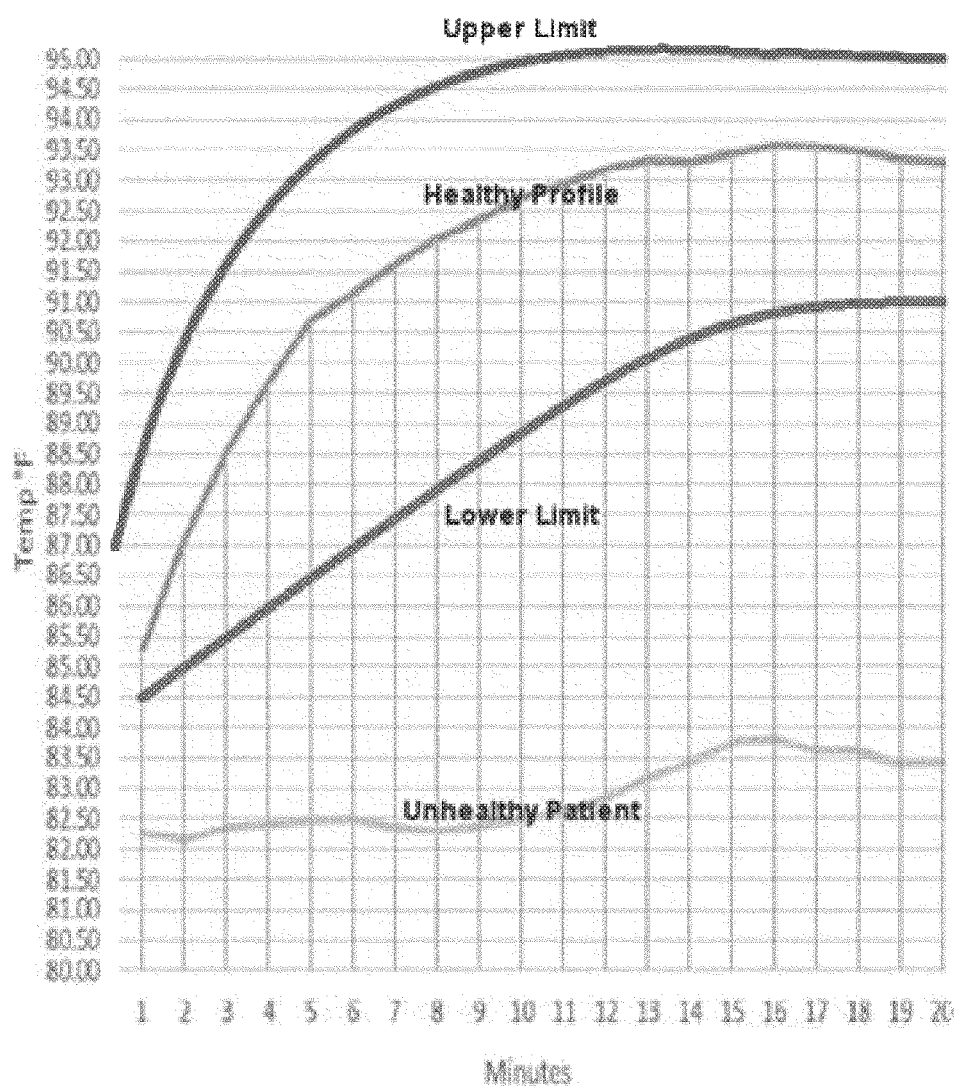
FIG. 6 is a graph illustrating energy transfer between the treatment hand and the non-treatment hand of a patient.

[1]AHI = AVACEN Health Index
[2]Total energy infused over a specific time period, e.g., 2 minutes at 10-minute point
[3]Energy transfer between the treatment hand and the non-treatment hand (FIG. 6).

Accordingly, programmable controller 270 may be configured to monitor and store data indicative of thermal energy transfer of a patient using thermal exchange device 200 for a treatment period, calculate a circulation rating for the patient based on the patient's estimated blood volume and thermal energy transfer over a specific period and/or at various locations throughout the body, and compare the patient's circulation rating with the baseline circulation rating that corresponds with the patient based on the patient's estimated blood volume. For example, a patient having an estimated blood volume calculated from the patient data measured by height recorder 102 and weight scale 106, and/or from age and/or gender based on the patient identity determined by patient identifier 108, will have their patient circulation rating compared against the baseline circulation rating of a healthy person having the same or similar blood volume.

Programmable controller 270 may be programmed to display the patient circulation rating via display 214, and/or send an alert, e.g., visual or audio alert, to a user, e.g., the patient or a clinician, via alert mechanism 278 if the patient circulation rating is below a predetermined threshold. The patient circulation rating may be alphanumeric, e.g., a letter score on a scale of A-F or a numerical score on a scale of 0-1 or 1-100. Programmable controller 270 may also be programmed to analyze the patient's circulation ratings over time to detect negative trends, and to send and alert via alert mechanism 278 if a negative trend is detected. As such, system 100 may predict cardiovascular issues based on early detection of negative trends.

Programmable controller 270 further may be programmed to send an alert, e.g., visual or audio alert, to a user, e.g., the patient or a clinician, via alert mechanism 278 if the patient's oxygen saturation measured by oximeter 122 falls outside a predetermined threshold, e.g., below 90% oxygen saturation, and/or if the patient's temperature at a specific location, e.g., temporal artery, measured by biometric patch 120 falls outside a predetermined threshold, e.g., below 96.8° F.

In one embodiment, multiple patients may have access to the thermal exchange device 200. Thus, programmable controller 270 may be programmed to calculate and store patient-specific circulation ratings in memory 276 based on the patient identity determined using patient identifier 108.

Programmable controller 270 preferably also includes preprogrammed safety features, e.g., that shutdown the device if the apparatus sensors, such as temperature and negative pressure sensors disposed within thermal exchange device 200, fail or become disconnected. Programmable controller 270 also may include an error circuit that displays error codes on display 214.

Programmable controller 270 may be programmed to direct thermal exchange member 204 to heat or cool to a temperature responsive to biometric patch data, user input at control panel 206 or to a preselected therapy regime. In one embodiment, programmable controller 270 is programmed to heat thermal exchange member to a high, medium, or low temperature, e.g., 109.4° F., 108.4° F., or 107.4° F., respectively, based on user input received at control panel 206. Programmable controller 270 further may include a clock application that directs thermal exchange member to heat or cool at the temperature for a time. e.g., 5, 10, 15, 20, 25, or 30 minutes, responsive to user input at control panel 206 or to a preselected therapy regime.

Figure 1B:
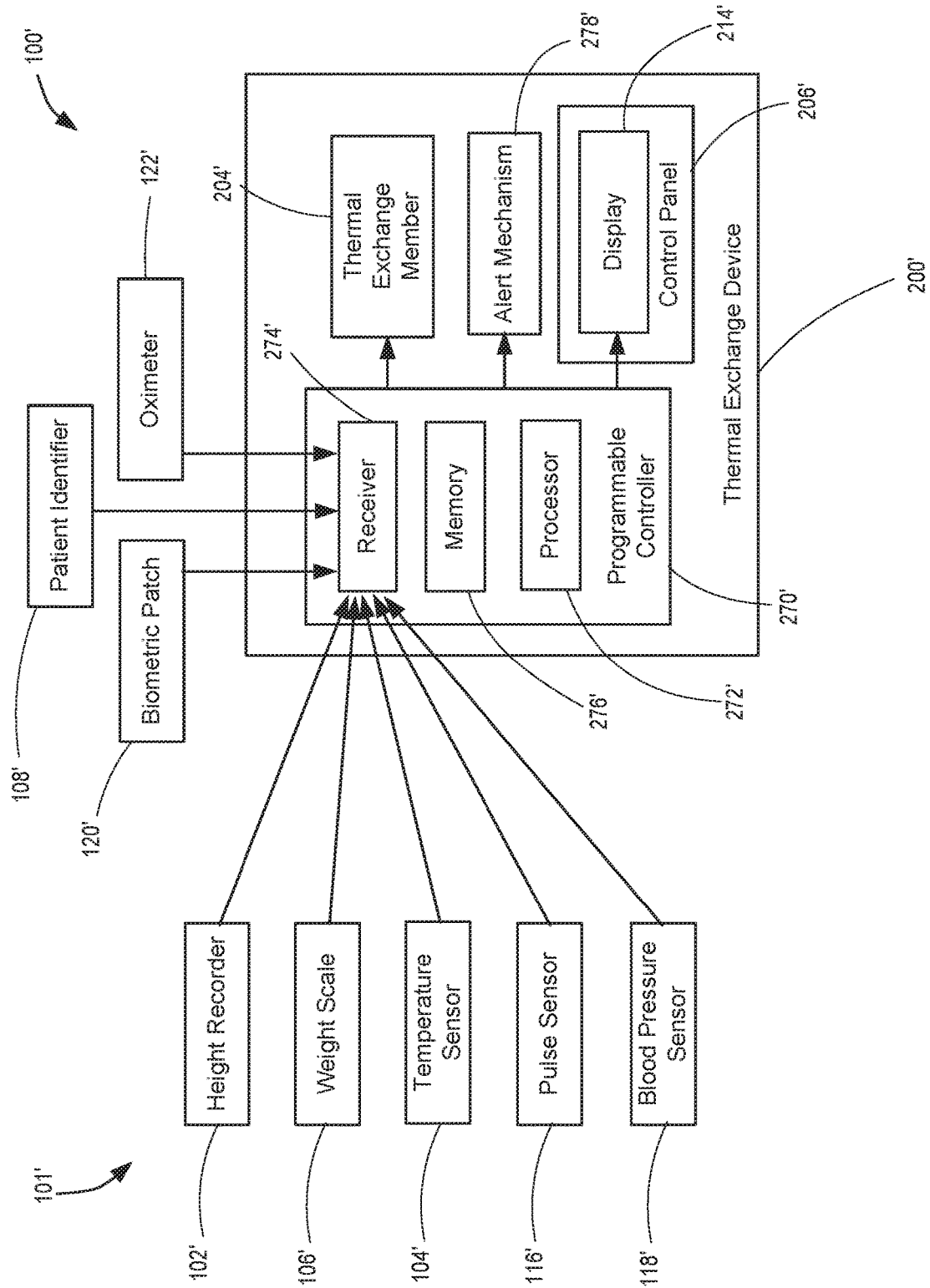

Referring now to FIG. 1B, a schematic illustrating an alternative exemplary blood evaluation system 100' for treating a condition constructed in accordance with one aspect of the present invention is described. Similar to system 100 of FIG. 1A, system 100' of FIG. 1B includes measurement device collection 101' and thermal exchange device 200'. Measurement device collection 101' includes, separately or together in a common housing, height recorder 102', temperature sensor 104', weight scale 106', pulse sensor 116', and/or blood pressure sensor 118', and thermal exchange device 200' includes programmable controller 270', thermal exchange member 204', control panel 206, alert mechanism 278', and display 214'. System 100' further may include patient identifier 108', biometric patch 120', and oximeter 122'.

System 100' of FIG. 1B is distinct from system 100 of FIG. 1A in that the data collection hub is integrated with programmable controller 270' such that height recorder 102', temperature sensor 104', weight scale 106', pulse sensor 116', blood pressure sensor 118', patient identifier 108', biometric patch 120', and oximeter 122', each directly transmit signal(s) indicative of the measured/input data to receiver 274' of programmable controller 270'.

Figure 2:
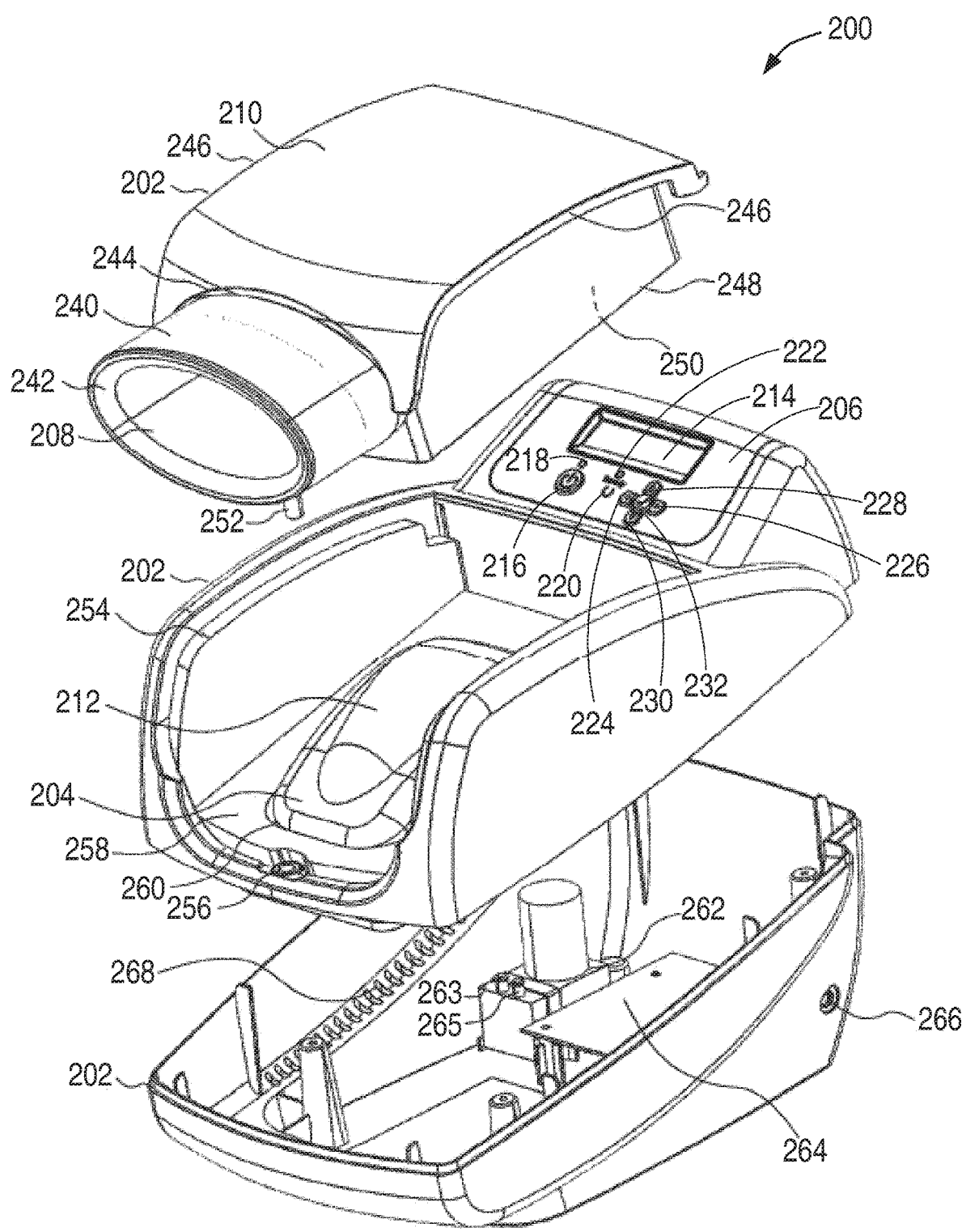
FIG. 2 is a perspective, partially exploded view of the exemplary thermal exchange device of FIGS. 1A and 1B.

Referring now to FIG. 2, an exemplary thermal exchange device is provided. Thermal exchange device 200 may communicate with devices of measurement device collection 101 directly or via data collection hub 110. As described in FIGS. 1A & 1B, thermal exchange device 200 includes thermal exchange member 204, control panel 206, display 214, alert mechanism 278, and programmable controller 270 having processor 272, receiver 274, and memory 276. Thermal exchange device 200 further may include appendage chamber 202, thermal exchange member 204, and control panel 206, and may be constructed as described in commonly assigned U.S. patent application Serial No. 2016/0022476, the entirety of which is hereby incorporated by reference. Appendage chamber 202 includes a housing sized and shaped to accept a human appendage containing an AVA such as a hand, for example, through appendage opening 208, which may also facilitate a blood pressure and pulse sensor. In preferred embodiments, appendage chamber 202 includes a durable and relatively rigid plastic or metal alloy, or combination thereof, of which individual components may be formed using conventional injection-molding or stamping processes. Appendage chamber 202 preferably includes pressure chamber insert (PCI) 210 that may be partially or fully transparent such that a user and/or physician may monitor the hand during treatment. Preferably, PCI 210 includes a rigid, substantially transparent plastic or polymer, such as polycarbonate, which allows the user or care-giver to visualize placement of the hand within the chamber.

Thermal exchange member 204 may be disposed within appendage chamber 202 and may include a plastic, biocompatible metal, such as aluminum, metal alloy, or the like. Thermal exchange member 204 is configured to selectively heat or cool blood flowing through the AVA of the appendage disposed within appendage chamber 202. For example, thermal exchange member 204 may be configured to be heated to approximately 107.4° F., 108.4° F., 109.4° F., between 107-110° F., between 105-112° F., or between 100-120° F., and may be configured to be cooled to approximately 60.8° F., between 60-62° F., between 58-64° F., or between 58-95° F. In one embodiment, thermal exchange member 204 includes a Peltier device configured to heat and/or cool thermal exchange member 204. Thermal exchange member 204 also may include suitable components for resistive heating such as a conductive wire configured to receive an electrical current and release heat. Thermal exchange member 204 may be shaped and sized to contact an appendage, for example, a palm of the hand. In one embodiment, thermal exchange member 204 includes palm pad 212 (shown in FIG. 2) that extends outwardly from thermal exchange member 204 to promote enhanced contact with the palm.

Control panel 206 is configured to provide a user interface for a user and/or clinician or care-giver to control operations of thermal exchange device 200. Control panel 206 may include buttons, assorted lighting sources, e.g., LEDs, and/or a display, e.g., an LCD or LED readout, that may be a touch screen.

Appendage chamber 202 may include a plurality of feet, e.g., feet coupled to a front portion of the base of appendage chamber 202 and feet coupled to a rear portion of the base of appendage chamber 202. The plurality of feet may be configured to be adjusted to raise or lower a portion of appendage chamber 202. For example, the rear feet may be adjusted to increase the distance between the rear feet and the base of appendage chamber 202, thereby raising the rear portion of thermal exchange device 200. In one embodiment, the rear feet are coupled to the base of appendage chamber 202 via a threaded male member that is screwed into a threaded female member in appendage chamber 202 to adjust the distance between the rear feet and the base of appendage chamber 202. Advantageously, a user may adjust the rear feet such that appendage opening 208 is angled in a manner that the user may insert their hand into appendage opening 208 and comfortably rest their elbow on a surface, e.g., table, desk, or medical cart, holding thermal exchange device 200.

As depicted in FIG. 2, PCI 210 may include appendage opening 208, cuff 240, expandable cuff 242, cuff seal 244, PCI edges 246, PCI base 248, PCI base opening 250, and positive pressure input 252. Cuff 240 may include a plastic, biocompatible metal, such as aluminum, metal alloy, or the like and is shaped and sized to accept an appendage through appendage opening 208. Illustratively, cuff 240 is elliptically shaped although, as would be understood by one of ordinary skill in the art, cuff 240 may take other shapes including a rectangle or a rectangle with rounded corners. Cuff 240 is coupled to expandable cuff 242. Expandable cuff 242 is configured to expand to seal around an appendage placed within PCI 210 through appendage opening 208. Expandable cuff 242 may include a rubber, such as latex, nitrile, or neoprene, and/or plastic, such as polyvinyl chloride, polyethylene, or polyurethane and may be between 1-20 mil thick, preferably about 2 mil. Cuff 240 may be coupled to the main body of PCI 210 via cuff seal 244. Cuff seal 244 is configured to couple cuff 240 to the main body of PCI 210, and may include a suitable sealing material such as tape. Cuff 240 optionally may be removable from PCI 210.

In accordance with one aspect of the present invention, PCI 210 is configured to be removable from appendage chamber 202. PCI 210 may be coupled to appendage chamber 202 by placing PCI edges 246 on chamber ledges 254 of appendage chamber 202 such that PCI base 248 contacts appendage chamber 202, optionally at sealing gasket 258, and thermal exchange member 204 is disposed within PCI base opening 250. PCI positive pressure input 252 is configured to be disposed within chamber aperture 256 of appendage chamber 202.

Illustratively, control panel 206 includes display 214, on/off button 216, on/off LED 218, ready symbol 220, ready LED 222, left button 224, right button 226, up button 228, down button 230, and accept button 232.

Thermal exchange device 200 further may include sealing gasket 258 that is configured to couple to PCI base 248 to maintain negative pressure within PCI 210 when PCI 210 is attached to appendage chamber 202. Sealing gasket 258 is disposed within appendage chamber 202. Although FIG. 2 depicts sealing gasket 258 coupled to the base of appendage chamber 202, sealing gasket 258 may alternatively be coupled directly to PCI base 248 when PCI 210 is removed from appendage chamber 202. Preferably, sealing gasket 258 includes a deformable material that supports PCI base 248 when it contacts sealing gasket 258 to create an air-tight seal. In one embodiment, sealing gasket 258 includes a groove that accepts PCI base 248 therein.

Pressure source 262 and circuitry housing 264 having a programmable controller coupled thereto may be disposed within appendage chamber 202. Pressure source 262 is a suitable device for pumping fluid, e.g., air, and for creating and maintaining negative pressure in appendage chamber 202 at a suitable pumping rate, e.g., greater than about 4 liters per minute. In one embodiment, pressure source 262 is a diaphragm pump. Pressure source 262 may be configured to apply positive pressure to expand expandable cuff 242 to seal around an appendage placed therein by pumping a fluid into expandable cuff 242. Pressure source also may be configured to apply negative pressure within appendage chamber 202, including PCI 210, and to create an air-tight seal between PCI base 248 and sealing gasket 258 when an appendage is placed therein. Preferably, as illustrated, pressure source 262 includes a single motor-driven pump configured simultaneously to apply negative pressure to the appendage and to selectably apply positive pressure to expand expandable cuff 242 when the appendage is placed within appendage chamber 202. For example, the pump may simultaneously apply negative pressure within the appendage chamber and positive pressure within the cuff, may selectably apply negative pressure only, and/or may selectably apply positive pressure only. Cuff 242 may also contain sensors to monitor blood pressure and pulse. Pressure source 262 may include positive pressure connector 263 and negative pressure connector 265. Positive pressure connector 263 includes a suitable coupling mechanism, illustratively a male protrusion, for coupling to a positive pressure line. Pressure source 262 may be coupled to expandable cuff 242 via the positive pressure line coupled between positive pressure connector 263 of pressure source 262 and PCI positive pressure input 252. Negative pressure connector 265 includes a suitable coupling mechanism, illustratively a male protrusion, for coupling to a negative pressure line. Pressure source 262 may be coupled to appendage chamber 202, including to PCI 210, via the negative pressure line coupled between negative pressure connector 265 of pressure source 262 and a negative pressure opening beneath thermal exchange member 204 such that pressure source 262 may apply negative pressure within appendage chamber 202, including within PCI 210, through the negative pressure opening. Advantageously, in an embodiment wherein pressure source 262 is a single motor-driven negative pressure pump, exhaust from the pump may be used to selectably expand expandable cuff 242 via the positive pressure line while the pump applies negative pressure within appendage chamber 202, including within PCI 210, via the negative pressure line. In one embodiment, pressure source 262 is configured to maintain the negative pressure within the appendage chamber between −20 mmHg and −40 mmHg or between −1 mmHg and −50 mmHg. Pressure source 262 assists in maintaining vasodilation and to enhance the transfer to energy to an arteriovenous anastomosis vascular area of the appendage, e.g., located in the palm of a hand. The arteriovenous anastomosis vascular area may experience vasodilation from pre-treatment hyper-normothermia and/or heat delivered to the area from thermal exchange member 204 during treatment.

Appendage chamber 202 may include power interface 266 that connects to an AC or DC power source to power thermal exchange device 200 and/or charge at least one battery within appendage chamber 202. In one embodiment, thermal exchange device 200 is powered with at least one replaceable battery and power interface 266 may be omitted.

Appendage chamber 202 may further include a plurality of vent holes 268 configured to expel heat resulting from operation of thermal exchange device 200 therethrough.

The electronics of thermal exchange device 200 are coupled to control panel 206, so that programmable controller 270 actuates thermal exchange device 200 in accordance with input commands or selection of pre-programmed therapy regimes input via control panel 206. For example, when programmable controller 270 detects that left button 224 or right button 226 is pressed, programmable controller 270 directs thermal exchange member 204 to decrease or increase temperature, respectively. As another example, when programmable controller 270 detects that up button 228 or down button 230 is pressed, programmable controller 270 directs a clock application to increase or decrease, respectively, a countdown timer for treatment.

Figure 3:
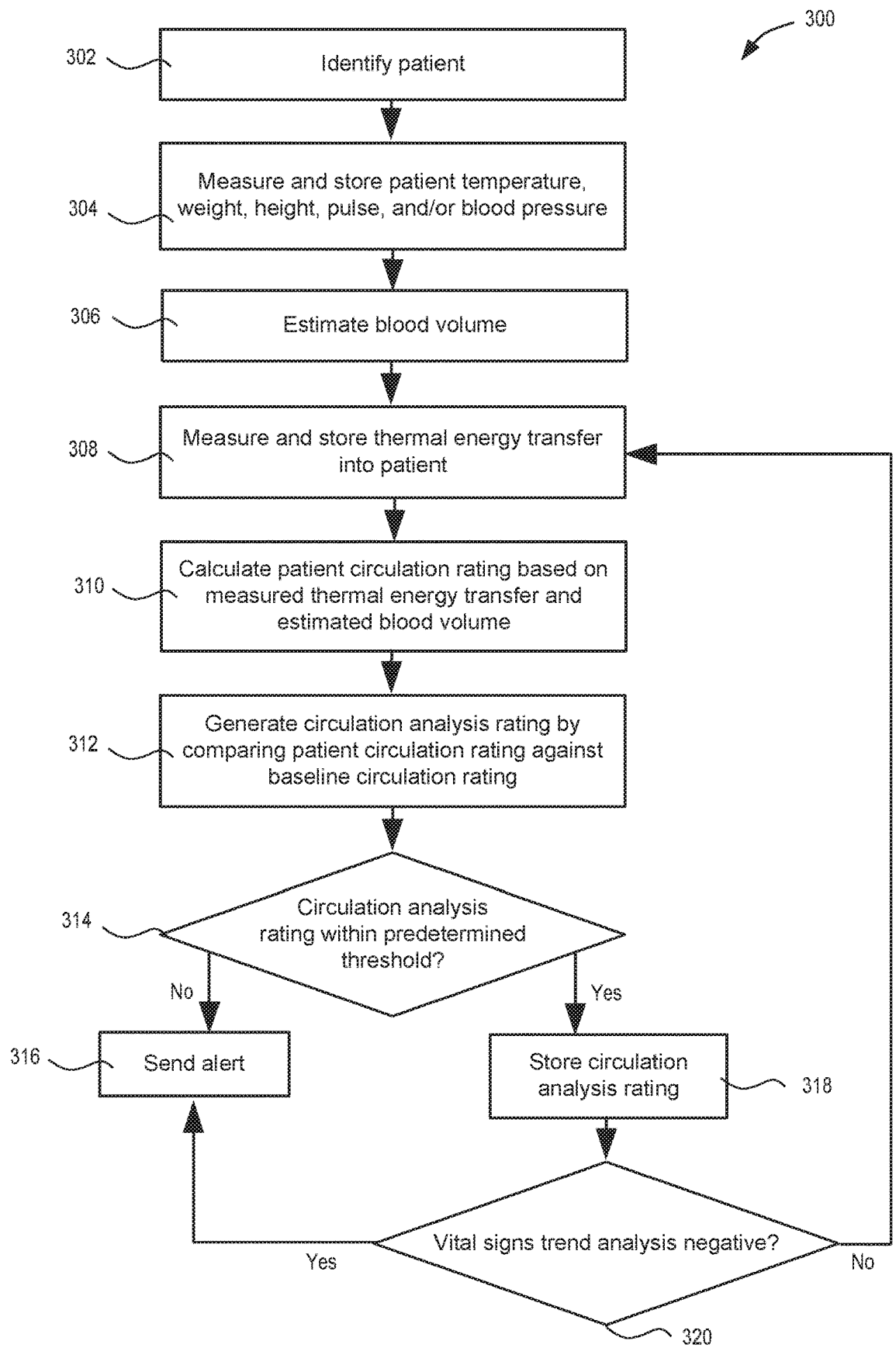
FIG. 3 is a flowchart depicting an exemplary method for evaluating blood circulation in accordance with the methods of the present invention.

Referring now to FIG. 3, exemplary method 300 for evaluating blood circulation is described. At step 302, the identity of the patient is determined using patient identifier 108. As described above, the patient identifier may identify the patient by, for example, scanning the patients' retina blood vessel pattern via a retinal scanner, receiving user input via a data entry interface, or by scanning a bar code or QR code. Patient identity may also include the patient's age and/or gender, which may be previously entered and stored in memory 276 for each patient. At step 304, patient information including height, temperature, weight, pulse, fitness level, and/or blood pressure may be measured or input via height recorder 102, temperature sensor 104, weight scale 106, patient identifier 108, pulse sensor 116, and/or blood pressure sensor 118, respectively. Signal generator 112 of data collector hub 110 may generate a signal indicative of the measured patient information and transmit the signal to thermal exchange device 200 via transmitter 114.

At step 306, the patient's blood volume is estimated based on the collected patient information. For example, signal generator 112 may be programmed to estimate the patient's blood volume directly from the patient information received from height recorder 102 and weight scale 106, and optionally the patient's age and/or gender and/or fitness based on the patient's identity received from patient identifier 108, and generate a signal indicative of the estimated blood volume for transmission to thermal exchange device 200 via transmitter 114 to receiver 274. In another embodiment, programmable controller 270 may be programmed to cause processor 272 to estimate the patient's blood volume based on the signal indicative of the patient information received from data collection hub 110, and optionally the patient's age and/or gender and/or fitness stored in memory 276 based on the patient's identity received from patient identifier 108.

At step 308, programmable controller 270 directs thermal exchange device 200 to provide the functionality ascribed to them herein, e.g., apply and monitor thermal energy transfer to an appendage of the patient within appendage chamber 202 using thermal energy member 204. For example, thermal exchange device 200 may monitor the amount of heat transfer from thermal exchange member 204, by measuring the change in temperature measured over time and/or at various locations throughout the body as indicated by biometric patch 120. For example, thermal exchange device 200 may measure the time it takes to raise the temperature of a specific location of the patient by a predetermined amount as measured by biometric patch 120. The monitored thermal energy transfer may be stored in memory 276.

At step 310, processor 272 of programmable controller 270 calculates a patient circulation rating based on the patient information measured during step 304 and the thermal energy transfer monitored and stored during steps 308 and/or 309. For example, the patient circulation rating may be calculated by dividing the thermal energy transfer (Joules/Infused), e.g., measured for two minutes after plateau for two minutes, by the estimated blood volume (milliliters). At step 312, processor 272 of programmable controller 270 compares the patient circulation rating calculated during step 310 against a baseline circulation rating of a healthy person having the same or similar blood volume as the patient, the baseline circulation rating selected from an empirically derived database or graph of baseline circulation ratings stored within memory 276, as described below with respect to FIG. 4. Alternatively, the patient's current circulation rating may be compared to prior recorded levels for that patient to identify improvement (or lack thereof) between successive measurements.

In one embodiment, the patient circulation rating may be alphanumeric, and may be displayed via display 214 of thermal exchange device 200. At step 314, processor 272 of programmable controller 270 determines whether the patient circulation rating is within a predetermined threshold. For example, if the patient circulation rating is on a scale of 0-1, the predetermined threshold may be 0.65, or if the patient circulation rating is on a scale of 1-100, the predetermined threshold may be 65, or if the patient circulation rating is on a scale of A-F, the predetermined threshold may be a D. In one embodiment, the predetermined threshold may be calculated for each specific patient based on patient identity, measured patient information, and previous treatment data.

If processor 272 of programmable controller 270 determines that the patient circulation rating is not within the predetermined threshold, e.g., is more than a predetermined threshold different than the baseline circulation rating, at step 316, programmable controller 270 may direct alert mechanism 278 to generate an alert, e.g., a visual and/or audible alert and/or external transmission e.g. wireless transmission. If processor 272 of programmable controller 270 determines that the patient circulation rating is within the predetermined threshold, at step 318, programmable controller 270 may store the patient circulation rating within memory 276 based on the patient's identity.

At step 320, processor 272 of programmable controller 270 may compare a current patient circulation rating to previous circulation ratings for a given patient stored within memory 276 during step 318, and determine whether there is a negative trend. If processor 272 of programmable controller 270 determines that there is a negative trend, method 300 proceeds to step 316 and generates an alert via alert mechanism 278. In addition, programmable controller 270 may also cause display 214 to display diagnostics regarding the negative trend detected at step 320. Accordingly, blood evaluation system 100 may predict cardiovascular issues based on the diagnostics. If processor 272 of programmable controller 270 does not determine that there is a negative trend, method 300 returns to step 308 and programmable controller 270 continues to direct thermal exchange device 200 to provide the functionality ascribed to them herein.

Figure 4:
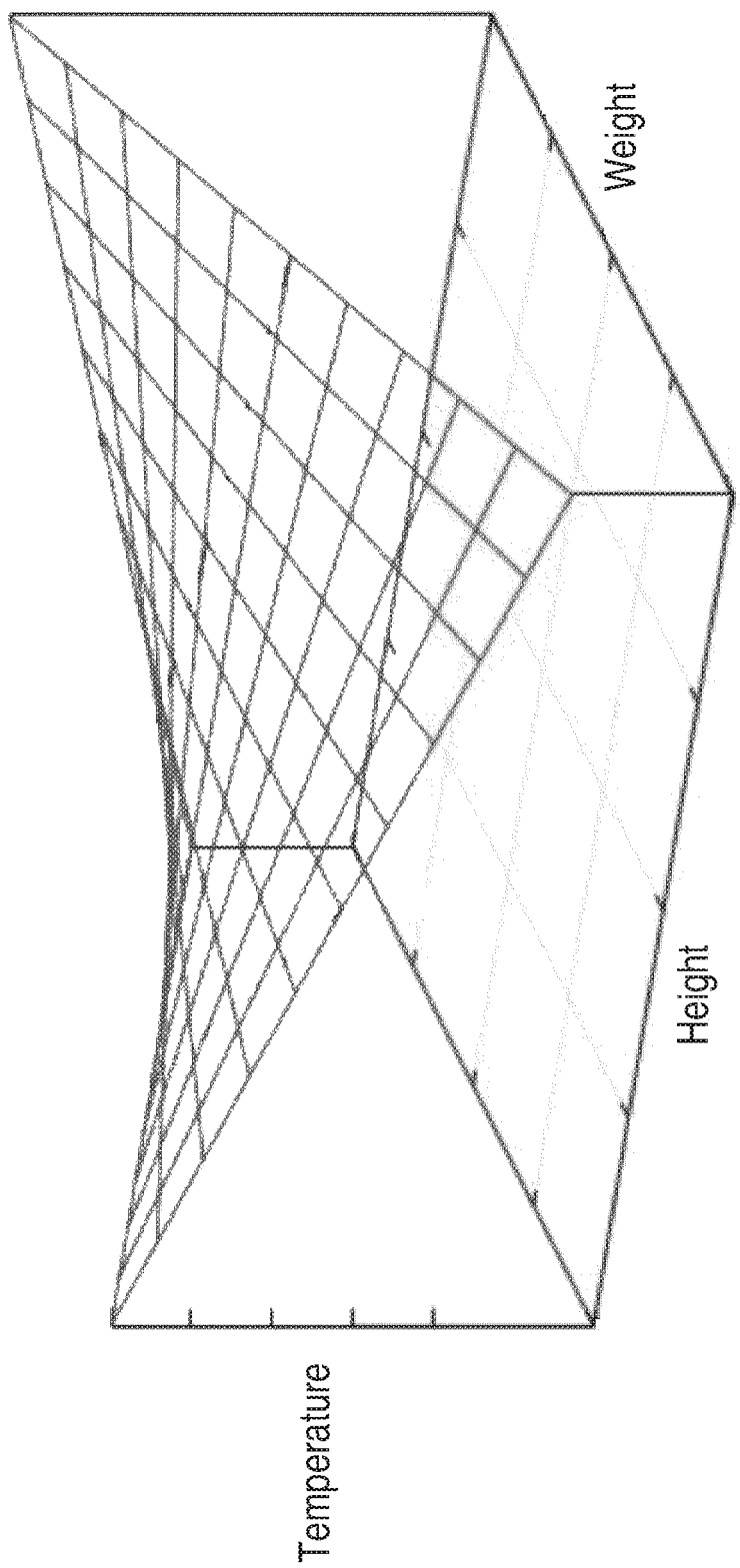
FIG. 4 is an empirically derived three-dimensional surface corresponding to preferred values of patient circulation ratings based on measured patient information.

FIG. 4 illustrates an empirically derived three-dimensional surface corresponding to preferred values of patient circulation ratings based on measured and/or inputted patient information, e.g., height, weight, age, gender, and fitness, for which a patient's blood volume may be estimated by either data collection hub 110 or processor 272 as described above. For example, for a given height and weight measurement measured by measurement device collection 101, and optionally the patient's age and/or gender and/or fitness based on patient identity determined by patient identifier 108, a baseline value for a specific patient's blood circulation rating may be determined.

Figure 5:
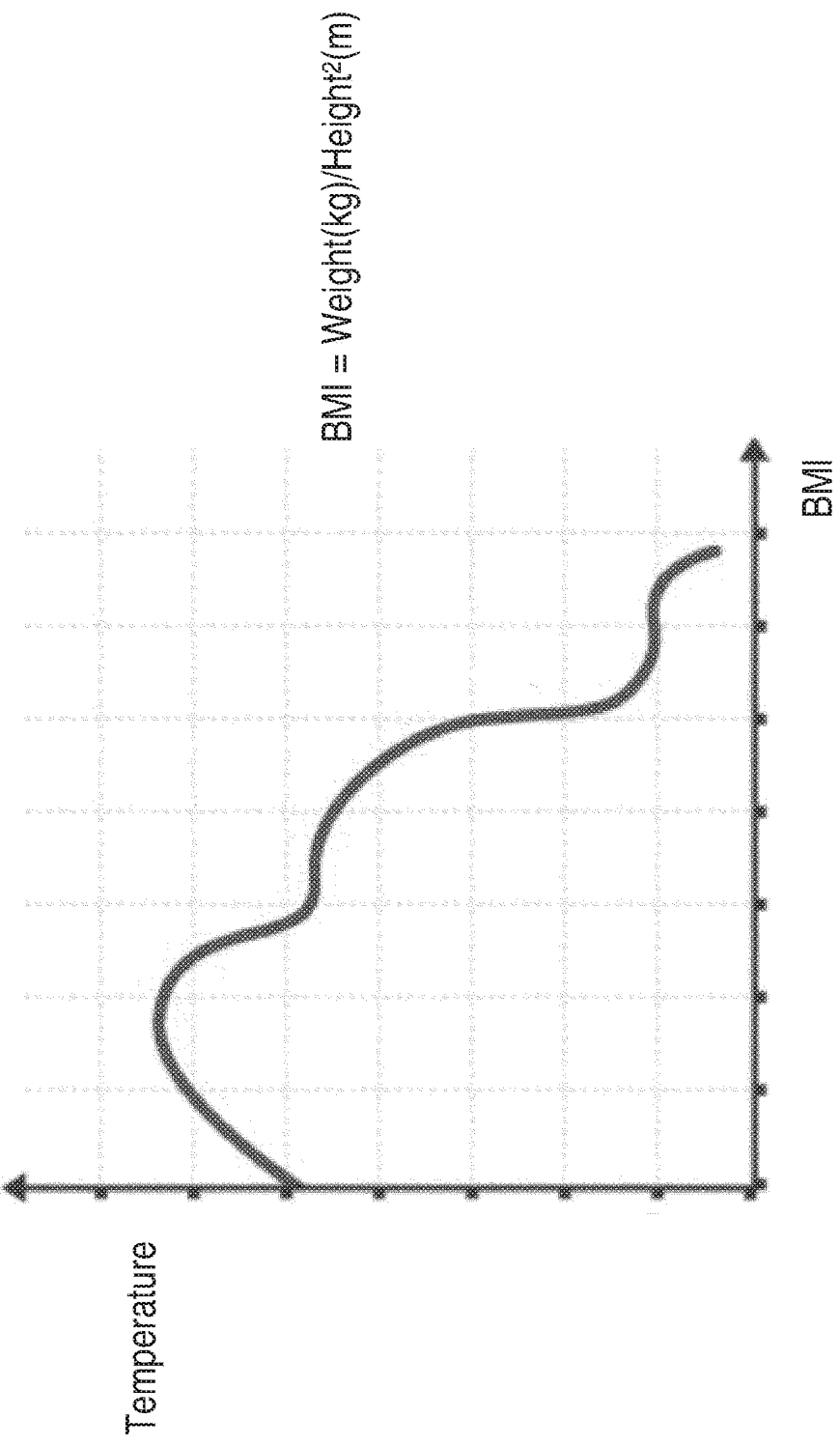
FIG. 5 is a two-dimensional graph depicting an alternative representation of an empirically derived database of baseline circulation ratings as a function of patient information.

FIG. 5 is a two-dimensional graph depicting an alternative representation of an empirically derived database of baseline circulation ratings as a function of patient information, e.g., body mass index (BMI), for which a patient's blood volume may be estimated by either data collection hub 110 or processor 272 as described above. A patient's BMI may be calculated by either data collection hub 110 or processor 272 as a function of the patient's height and weight. For example, for a given BMI and weight measurement measured by measurement device collection 101, and optionally the patient's age and/or gender based and/or fitness on patient identity determined by patient identifier 108, a patient may be predicted to have an optimum blood circulation rating within a specified threshold, e.g., plus or minus 10% of the value of the curve specified in FIG. 5 for a specific BMI.

While various illustrative embodiments of the disclosure are described above, it will be apparent to one skilled in the art that various changes and modifications may be made therein without departing from the invention. The appended claims are intended to cover all such changes and modifications that fall within the true scope of the systems and methods of the present invention.

What is claimed:

1. A blood circulation evaluation system, the system comprising:
   an appendage chamber configured to accept a human appendage of a patient, the appendage containing an arteriovenous anastomosis (AVA);
   a thermal exchange member disposed within the appendage chamber, the thermal exchange member configured to selectively heat or cool blood flowing through the AVA and to monitor thermal energy transferred to blood flowing through the AVA;
   a pressure source coupled to the appendage chamber and configured to apply negative pressure within the appendage chamber;
   a processor operatively coupled to a memory; and
   non-transitory instructions stored in the memory that, when executed by the processor, cause the processor to:
      estimate a blood volume of the patient based on patient information comprising at least one of one or more patient physical characteristics or a patient identity;
      determine an amount of thermal energy transfer to the blood flowing through the AVA from the thermal exchange member during a specific time period; and
      calculate a patient circulation rating as a ratio of the amount of thermal energy transfer over the specific time period over the estimated blood volume.

2. The system of claim 1, wherein the memory stores a database of baseline circulation ratings for a pre-selected group of humans, each baseline circulation rating based on a corresponding patient-specific blood volume and corresponding patient-specific amount of thermal energy absorption over a predetermined time period of a corresponding human of the pre-selected group of humans, the processor further programmed to compare the patient circulation rating to a baseline circulation rating within the database selected based on the patient information to compute an indicia of patient cardiovascular health, and to send an alert if the indicia falls outside a predetermined range.

3. The system of claim 1, further comprising:
   a measurement device configured to collect patient information comprising at least one of patient height or weight; and
   a data hub operatively coupled to the measurement device, the data hub configured to generate a signal indicative of the measured patient information and transmit the signal to the processor.

4. The system of claim 3, wherein the measurement device further comprises one or more temperature sensors.

5. The system of claim 1, further comprising an input device configured to accept the patient identity.

6. The system of claim 5, wherein the input device is configured to accept data corresponding to a patient's age or gender.

7. The system of claim 3, wherein the data hub is configured to transmit the signal indicative of the measured patient information wirelessly.

8. The system of claim 1, further comprising a biometric patch configured to measure temperature and to generate a signal indicative of the measured temperature.

9. The system of claim 2, further comprising a display operatively coupled to the processor, the display configured to display the patient circulation rating or indicia.

10. The system of claim 1, wherein the processor stores in the memory a previously stored value of the circulation rating for the patient.

11. The system of claim 10, wherein the processor is further programmed to determine whether there is a negative trend in the patient circulation rating over time, and to send an alert if the negative trend is determined.

* * * * *